United States Patent [19]

Raspanti et al.

[11] Patent Number: 4,477,615

[45] Date of Patent: Oct. 16, 1984

[54] POLYPIPERIDINYL STABILIZING AGENTS FOR POLYMER MATERIALS

[75] Inventors: Giuseppe Raspanti; Norberto Fossati, both of Mozzo, Italy

[73] Assignee: Apital Produzioni Industriali S.p.A., Milan, Italy

[21] Appl. No.: 483,092

[22] Filed: Apr. 8, 1983

[30] Foreign Application Priority Data

May 19, 1982 [IT] Italy ............................... 21346 A/82

[51] Int. Cl.³ .................... C07D 403/14; C08G 73/04; C08G 73/00; C08K 5/34
[52] U.S. Cl. .................................. 524/100; 528/423; 544/198; 544/212
[58] Field of Search ....................... 524/100; 528/423; 544/198, 212

[56] References Cited

U.S. PATENT DOCUMENTS

| | | | |
|---|---|---|---|
| 3,925,376 | 12/1975 | Chalmers et al. | 524/101 |
| 4,086,204 | 4/1978 | Cassandrini et al. | 524/101 |
| 4,104,248 | 8/1978 | Cantatore | 528/423 |
| 4,315,859 | 2/1982 | Nikles | 524/100 |
| 4,433,145 | 2/1984 | Wiezer et al. | 544/198 |

Primary Examiner—Veronica P. Hoke
Attorney, Agent, or Firm—Walter H. Schneider

[57] ABSTRACT

The invention relates to novel polypiperidine compounds which give polymer materials high stability against oxidation and degradation when exposed to light, and to the process for the production thereof.

17 Claims, No Drawings

POLYPIPERIDINYL STABILIZING AGENTS FOR POLYMER MATERIALS

The invention relates to novel polypiperidine compounds and use thereof as stabilizing agents for polymers.

As is known, synthetic polymers may deteriorate through the action of heat, light or oxygen, which cause degradation, embrittlement, discloration and other undesirable effects.

Various classes of chemical compounds have been proposed for stabilizing polymer materials, mainly against UV radiation from sunlight. Examples of such compounds are benzophenones, benzotriazoles, α-cyanoacrylates.

These compounds give polymers an acceptable but not a practical stability, especially for fibers, films and raffia containing olefin polymers.

It has now been found that the novel polymeric compounds having the general formula I give polymer materials high stability against oxidation, particularly degradation when exposed to light.

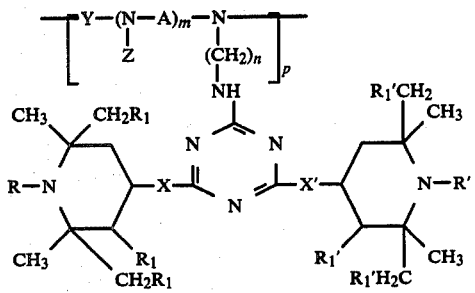
(I)

in which R and R' can be the same or different, and represent hydrogen, a straight-chain or branched-chain alkyl radical having 1 to 12 carbon atoms, an alkenyl radical having 3 to 8 carbon atoms, an aralkyl radical having 7 to 19 carbon atoms;

$R_1$ and $R'_1$ can be the same or different and represent hydrogen or methyl;

X and X' can be the same or different and represent oxygen or the group N—$R_2$ in which $R_2$ represents hydrogen, straight-chain or branched-chain alkyl having 1 to 12 carbon atoms, a cycloalkyl radical having 5 to 12 carbon atoms, an aralkyl radical having 7 to 12 carbon atoms;

n can be 2 to 12;

A represents —$(CH_2)_n$—, in which n has the previously defined meaning, the group:

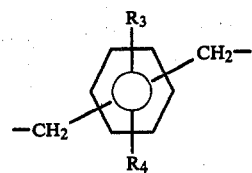

in which $R_3$ and $R_4$ are hydrogen or methyl, the group

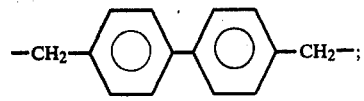

the group

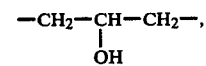

or the group —$CH_2$—$CH_2$—(O—$CH_2$—$CH_2$)$_a$— in which a can be 1–3;

Z represents hydrogen, an alkyl radical having 1 to 18 carbon atoms, a group of formula II

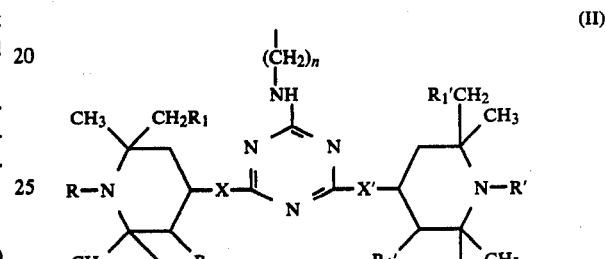
(II)

in which R, R', $R_1$, $R'_1$, X, X' and n have the previously defined meaning, or a piperidine group of formula III

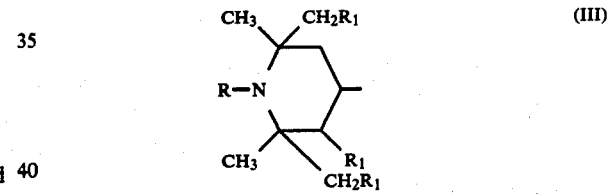
(III)

m can be equal to zero or 1;

Y, when m is zero, has the same meaning of A; when m is 1, can have the same meaning of A or represent the following groups

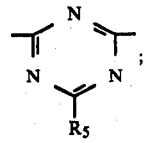

—CO—$R_6$—CO;   —CO—NH—$R_7$—NH—CO,
—COO—$R_8$—OOC—   —$H_2C$—$R_9$—CO— in which $R_5$ represents hydrogen, a straight-chain or branched alkyl radical having 1 to 18 carbon atoms, a cycloalkyl radical having 5 to 12 carbon atoms, an alkenyl radical having 3 to 18 carbon atoms, an optionally substituted aralkyl radical, having 7 to 19 carbon atoms, an aryl radical having 6 to 12 carbon atoms or the

O—$R_{11}$, S—$R_{11}$ groups, in which $R_{11}$ and $R_{10}$ can be the same or different and represent hydrogen, a straight-chain or branched alkyl radical having 1 to 18 carbon atoms, a cycloalkyl radical having 5 to 12 carbon atoms, an aralkyl radical having 7 to 12 carbon atoms, an aryl radical having 6 to 12 carbon atoms, $R_{11}$ and $R_{10}$ together with the nitrogen atom can form a 5 to 7 membered heterocyclic ring; or $R_5$ represents the piperidine group of formula IV

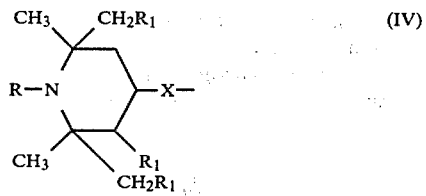

in which R, $R_1$ and X have the previously defined meaning;

$R_6$ represents a bivalent alkylene radical having 1 to 8 carbon atoms, the phenylene radical;

$R_7$ represents a bivalent alkylene radical having 2 to 6 carbon atoms, the tolylene radical, the xylene radical;

$R_8$ represents a bivalent alkylene radical having 2 to 8 carbon atoms;

$R_9$ represents an alkylene radical having 1 to 2 carbon atoms or a p-phenylene radical;

p can vary from 2 to 2000.

The following are examples of $R_1$ and $R'_1$: hydrogen, methyl, ethyl, propyl, butyl, hexyl, octyl, dodecyl, allyl, butenyl and benzyl.

The following are examples for A: ethylene, propylene, butylene, hexylene, octylene, dodecylene, 1,4-xylylene, 1,2-xylylene, 1,3-xylylene, dimethyl-xylylenes or mixtures thereof.

The following are examples for $R_2$: hydrogen, methyl, propyl, butyl, benzyl, hexyl, octyl, dodecyl, ciclohexyl.

The following are examples for $R_5$: hydrogen, methyl, ethyl, propyl, isopropyl, butyl, isobutyl, hexyl, octyl, dodecyl, allyl, butenyl, methylallyl, undecenyl, cyclopentyl, cyclooctyl, benzyl, methylbenzyl, dodecylbenzyl, phenyl, methylamino, ethylamino, propylamino, isopropylene-amino, butylamino, hexylamino, octylamino, dodecylamino, dimethylamino, diethylamino, dipropylamino, dibutylamino, oxymethyl, oxyethyl, oxybutyl, oxyoctyl, oxydodecyl, thiomethyl, thioethyl, thiopropyl, thiobutyl, thiooctyl, thiododecyl, morpholine, piperidine, hexamethyleni-mine, (2,2,6,6-tetramethyl-piperidin-4-yl)-amino; (2,2,6,6-tetramethylpiperid-4-yl)-ethylamino; (2,2,6,6-tetramethyl-piperid-4-yl)-butylamino; (1,2,2,6,6-pentamethylpiperid-4-yl)-ethylamino; (2,2,6,6-tetramethyl-piperid-4-yl)-oxy; (1-allyl-2,2,6,6-tetramethyl-piperid-4-yl)-oxy; (1-benzyl-2,2,6,6-tetramethyl-piperid-4-yl)-amino; (2,6-diethyl-2,3,6-trimethyl-piperid-4-yl)-amino.

A preferred sub-group of compounds according to the invention are those corresponding to formula V

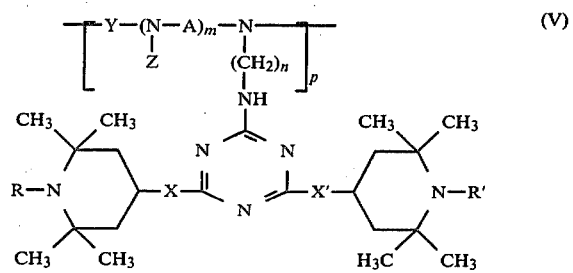

in which X, X', Y, Z, R, R', m, n, A and P have the previously defined meaning.

The invention also relates to the use of compounds having the general formula I as stabilizers for polymers.

Formula-I compounds are excellent stabilizers which give polymer materials, particularly polyolefins, very high stability against degradation caused by heat, oxygen or more particularly ultraviolet radiation from sunlight.

According to the invention, "polymers" denote polyethylenes, polypropylenes, polystyrenes, polybutadienes, polyisoprenes and copolymers thereof, polyvinyl chloride, polyvinylidene chloride and copolymers thereof, polyvinyl acetate and copolymers thereof, more particularly with ethylene, polyesters such as polyethylene terephthalate, polyamides such as Nylon 6 and Nylon 6,6 and polyurethanes.

Compounds according to formula I can be incorporated in polymers by any known method of mixing additives with polymers materials. For example, formula I compounds can be mixed with the polymer in a suitable mixer, or can be added in solution or suspension form in a suitable solvent such as methanol or ethanol or acetone, the solvent being removed after intimately mixing with the polymer, which can be in the form of a powder, granulate or suspension. Alternatively, formula I compounds can be added to the polymer during the preparation thereof, e.g. in the last stage of preparation.

Formula I compounds can also be added together with other kinds of commonly-used stabilizers and additives, e.g. anti-oxiding agents based on phenols, amines, phosphites, UV absorbers based on benzotriazoles and benzophenones, plasticizing agents, lubricants, antistatic agents, anti-flame agents or titanium oxide. The amount of formula I compounds required for efficient stabilization of the polymer depends on various factors, such as the type and characteristics of the polymer, the use for which it is intended, the intensity of radiation and the duration of exposure. Usually a quantity of 0.01 to 5% by weight of the polymer, preferably 0.1 to 1.0%, is sufficient.

The invention also relates to a method of preparing compounds having the general formula I. By reacting a compound of formula VI

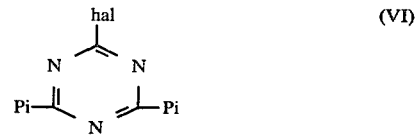

in which "hal" means halogen, preferably chlorine or bromine, and Pi is the piperidino group of formula IV, with a diamine of formula NH₂—(CH₂)ₙ—NH₂, a compound of formula VII

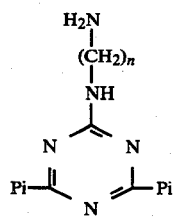

is obtained.

By reacting one mole of VII with one mole of a "hal—A—hal" compound, in which A has the previously defined meaning and "hal" is chlorine or bromine, compounds of formula I are obtained, when m is equal to zero and Y has therefore the same meaning of A.

By reacting 2 moles of VII with 1 mole of a "hal—A—hal" compound, compounds of formula VIII are obtained:

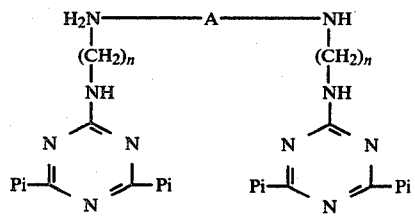

By reacting VIII with one of the following compounds

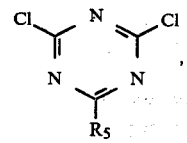

Cl—CO—R₆—COCl, OCN—R₇—NCO, ClCOO—R₈—OOC—Cl Cl—CH₂—R₉—COCl there are obtained compounds of formula I, in which m is 1 and Z is the group of formula II.

Compounds of formula I can be obtained by reacting VI with a triamine H₂N(CH₂)ₙ—NH—(CH₂)ₙ—NH—Z, in which Z is hydrogen or an alkyl group, thereby obtaining the compound of formula IX

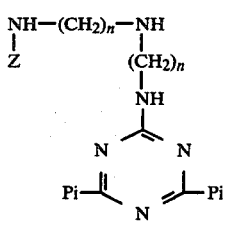

in which Z, n and Pi have the previously defined meaning.

By reacting IX with one of the following compounds

Cl—CO—R₆—COCl, OCN—R₇—NCO, ClCOO—R₈—OOC Cl, Cl—CH₂—R₉—COCl compounds of formula I, in which m is 1, are obtained.

Compounds having the formula VII are known and can be prepared by known methods.

Solvents such as toluene, xylene, acetone, dimethylformamide or other aprotic solvents can be used for the reaction. Preferably the reaction is performed in the presence of acid acceptors such as organic or inorganic bases, e.g. triethylamine, pyridine, sodium or potassium hydroxide, or sodium or potassium carbonate or bicarbonate.

The desired compounds are isolated and purified by known methods from the reaction mixture.

EXAMPLE 1

53.6 Grams (0.1 moles) of 2-chloro-4,6-bis-[(2',2',6',6'-tetramethyl-piperidin-4'-yl)-buthylamino]-1,3,5-triazine were suspended in 300 g of diethylenetriamine and heated to 110°–120° C. in inert atmosphere; the mixture was left to stand for 4 hours, under stirring; then it was cooled, 250 ml of toluene and 100 ml of 30% sodium hydroxide were added, the mixture was stirred for 15 minutes.

After the obtained phases have been separated, the organic phase was washed several times with water and dried over Na₂SO₄.

By evaporation of the solvent, 2-(1-diethylenetriamino)-4,6-bis-[(2',2',6',6'-tetramethyl-piperidin-4'-yl)butylamino]-1,3,5-triazine was obtained, in the form of a vitreous substance melting at 61°–63° C. 15 Grams (0.025 moles) of this compound were dissolved in 200 ml of DMF (dimethylformamide) and 7 g of 0.050M potassium carbonate were added to the solution; the resulting suspension was heated to 50° C. Then, under strong stirring, 8.3 g (0.023 moles) of 2,4-dichloro-6-[(2',2',6',6'-tetramethyl-piperidin-4'-yl)-butylamino]-1,3,5-triazine, dissolved in 80 ml of DMF, were added dropwise in 10 minutes, and the reaction mixture was maintained at 50° C. for 1 hour. After heating till 100° C. for 5 hours, the temperature was raised to 130° C. for 3 hours.

Then the reaction was stopped, the reaction mixture was poured in 1000 g of water and ice: a white precipitate was obtained, which was extracted with diethyl ether. The ethereous phase was separated, washed with much water and finally dried over Na₂SO₄, the solvent was evaporated off and the resulting residue was dried at 0.03 torr and 120°–130° C. for 3 hours.

A colourless resin was thus obtained, having m.p. at 158°–190° C.

A purification carried out dissolving the product in DMF and precipitating by dilution with acetonitrile, yielded a colourless resin with m.p. 160°–210° C., which showed, in a 1% by weight solution of 1,2-dichloroethane, a specific viscosity of 0.059.

EXAMPLE 2

93 Grams (0.174 moles) of 2-chloro-4,6-bis-[(2',2',6',6'-tetramethyl-piperidin-4'-yl)-butylamino]-

1,3,5-triazine and 25.4 g (0.074 moles) of triethylamine were dissolved in 1000 ml of dioxan and then 8.4 g (0.21 moles) of caustic soda in 24 ml of distilled water were promptly added; the reaction mixture was heated to reflux; after 24 hours a part of the dioxane was distilled off and substituted by water, thus obtaining a doughy precipitate which was extracted with ether.

The ethereous phase was washed throughly with water and finally dried over $Na_2SO_4$.

By removing the solvent, 1,10-bis-[4',6'-di-(2'',2'',6'',6''-tetramethyl-piperidin-4'''-yl)-butylamino]-1,3,5-triazin-2'-yl]-triethylentriamine was obtained, with m.p. 93°–95° C., in the form of a vitreous substance.

From 14.5 g (0.0127 moles) of said substance and 4.2 g (0.0117 moles) of 2,4-dichloro-6-[(2',2',6',6'-tetramethylpiperidin-4'-yl)-butylamino]-1,3,5-triazine, by operating in the same way as described in example 1, an almost colourless resin was obtained; m.p. 143°–150° C., whose specific viscosity in a 1% by weight 1,2-dichloroethane solution, was 0.055.

butylamino]-1,3,5-triazine were dissolved in 150 ml of n-hexane, and the solution was taken to 10° C.

Then 4.0 g (0.0237 moles) of hexamethylendiisocyanate were added dropwise, in 10 minutes, between 10° and 15° C., under stirring.

A white solid immediately precipitated, the mixture was again stirred for 2 hours, then it was heated to reflux for 1 hour, cooled, filtered and dried at 0.03 Torr and 120°–130° C. for 3 hours. A white powder was obtained, with m.p. 155°–180° C., whose specific viscosity in a 1% by weight 1,2-dichloroethane solution was 0.083.

EXAMPLE 8

By operating in the same way, from hexamethylenediisocyanate and 1,10-bis-[4',6'-[(2'',2'',6'',6''-tetramethyl-piperidin-4'''-yl)-butylamino]-1,3,5-triazin-2'-yl]-triethylenetetramine, a colourless resin was obtained, with m.p. 126°–150° C., whose specific viscosity in a 1% by weight 1,2-dichloroethane solution was 0.085.

TABLE 1
EXAMPLES 3-6
By operating in the same manner there were obtained the compounds of formula

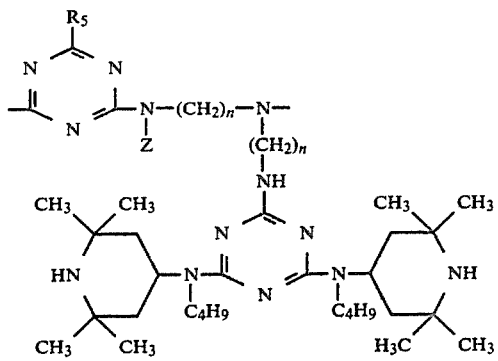

in which

| EXAMPLE | $R_5$ | Z | M.P. (°C.) | SPECIFIC VISCOSITY IN 1% BY WEIGHT SOL. | solvent |
|---|---|---|---|---|---|
| 3 | ter.$C_8H_{17}N$ | H | softens at 250–260° C., over 280° C., begins to release gas | 0.055 | DMF |
| 4 | $C_8H_{17}$ | H | 102–105 | 0.057 | 1,2-DICHLOROETHANE |
| 5 | S—$CH_3$ | H | 162–173 | 0.059 | " |
| 6 | S—$CH_3$ | —(CH₂)₂—NH—[structure with C₄H₉, tetramethylpiperidine groups] | 150–160 | 0.058 | " |

EXAMPLE 7

15 Grams (0.0250 moles) of 2-(1-diethylenetriamino)-4,6-bis-[(2', 2',6',6'-tetramethyl-piperidin-4-yl)-

EXAMPLE 9

15 Grams (0.0131 moles) of 1,10-bis-[4',6'-[(2'',2'',6'',6''-tetramethyl-piperidin-4'''-yl)-butylamino]-1,3,5-triazin-2'-yl]-triethylenetetramine and 1.26 g (0.0125 moles) of triethylamine were dissolved in 150 ml of toluene.

Then 3.03 g (0.0125 moles) of 1,6-hexandiol dichloroformiate, dissolved in 30 ml of toluene, were added dropwise in 10 minutes, at room temperature, under stirring.

The reaction mixture was stirred again for 2 hours, then it was heated to 50°–60° C. and stirred again for 3 hours. After cooling, the solvent was distilled off under vacuum. The residue was thoroughly washed with distilled water, filtered and dried at 120°–130° C. and 0.03 Torr for 3 hours.

A white powder with m.p. 235°–245° C. was obtained, whose specific viscosity in a 1% by weight DMF solution was 0.068.

EXAMPLE 10

16 Grams (0.027 moles) of 2-(1'-diethylenetriamino)-[4,6-[2'',2'',6'',6''-tetramethyl-piperidin-4''-yl)-butylamino]-1,3,5-triazine and 5.3 g (0.052 moles) of triethylamine were dissolved in 200 ml of DMF, then 4.3 g (0.023 moles) of adipoylchloride in 50 ml of DMF were added dropwise in 1 hour, at 25° C.

Then the mixture was heated to 50° and stirred for 3 hours, and the temperature was raised to 70° C. Stirring was carried out for 1 hour, then the reaction mixture was cooled and poured in 1 l of distilled water, at 50° C., and a semi-solid mass was separated which was extracted with 1,2-dichloroethane.

By distilling off the solvent, an ivory coloured powder was obtained, which could be purified by dissolving in DMF and precipitating with CH$_3$CN and was finally dried at 120°–130° C. and 0.03 Torr for 3 hours. A compound, with a specific density in 1% by weight 1,2-dichloroethane was 0.088, was obtained.

EXAMPLE 11

10.00 Grams (0.0087 Moles) of 1,10-bis-[4,6-[(2'',2'',6'',6''-tetramethyl-piperidin-4''-yl)-butylamino]-1,3,5-triazin-2'-yl)]-triethylenetetramine were dissolved in 100 ml of DMF, in which 2.40 g (0.0174 moles) of potassium carbonate had been suspended.

Then 1.45 g (0.0083 moles) of 1,4-di-(chloromethyl)-benzene, dissloved in 20 ml of DMF, were added dropwise in 10 minutes, under stirring. The reaction mixture was then heated till 90° C., stirred for 5 hours, cooled and poured in 500 ml of water. The resulting precipitate was extracted with 1,2-dichloroethane, the phases were separated and the organic phase was washed with much water. After elimination of the solvent, the compound was purified as usually, obtaining a slightly yellowish resin with m.p. 145°–168° C., which showed a specific viscosity of 0.065, in a 1% by weight solution of 1,2-dichloroethane.

EXAMPLE 12

10 Grams (0.0087 Moles) of 1,10-bis-[4,6-[(2'',2'',6'',6''-tetramethyl-piperidin-4''-yl)-butylamino]-1,3,5-triazin-2'-yl]-trietilamine were dissolved in 100 ml of DMF, in which 2.40 g (0.0174 moles) of potassium carbonate were suspended. Then 0.77 g (0.0083 moles) of epichloridrine dissolved in 10 ml of DMF were added dropwise, in 10 minutes, under stirring.

The reaction mixture was left at room temperature for 1 hour, heated to 90° C. and left to stand for 5 hours, then cooled and poured in 500 ml of distilled water, filtered and washed with much distilled water.

After drying and possibly purification, a colourless resin with m.p. 105°–120° C., was obtained, which showed a specific viscosity of 0.049 in a 1% by weight solution of 1,2-dichloroethane.

EXAMPLE 13

9 Grams (0.0160 moles) of 2-ethylenediamino-4,6-bis-[(2',2',6',6'-tetramethyl-piperidin-4'-yl)-butylamino]-1,3,5-triazine were dissolved in 100 ml of DMF in which 2.20 g (0.0160 moles) of potassium carbonate had been suspended.

Then 1.40 g (0.008 moles) of 1,4-di-chloromethyl-benzene dissolved in 10 ml of DMF were added, under stirring, in 10 minutes. The reaction mixture was heated to 90° C. and left to stand for 5 hours, then it was cooled to 50° C., and 2.20 g (0.0160 moles) of potassium carbonate were added and 2.70 g (0.0075 moles) of 2,4-dichloro-6-[(2',2',6',6'-tetramethyl-piperidin-4'-yl)-butylamino]-1,3,5-triazine were added dropwise in 10 minutes, under stirring. Stirring was continued for 1 hour again. Then the temperature was raised till 110° C., under stirring, for 5 hours, then till 120° C. for 5 more hours are finally the mixture was cooled. After the usual recovering and purification operations, a pale yellow resin was obtained, having m.p. 138°–147° C. and a relative viscosity of 0.059, in a 1% by weight solution of 1,2-dichloroethane.

EXAMPLE 14

9 Grams (0.016 moles) of 2-ethylenediamino-4,6-bis[(2',2',6',6'-tetramethyl-piperidin-4'-yl)-butylamino]-1,3,5-triazin-2'-yl-triethylenetriamine were dissolved in 100 ml of DMF, in which 4,4 g (0.032 moles) of potassium carbonate were suspended. Then 2.63 g (0.015 moles) of 1,4-di-chloromethyl-benzene in 20 ml of DMF were added dropwise, in 10 minutes, under stirring. The reaction mixture was heated to 90° C. and left to stand for 5 hours, then the temperature was raised till 120° C. and stirring was carried out for 6 hours. After the usual recovering and purification operations, a colourless resin with m.p. 134°–148° C. was obtained, whose specific viscosity, in a 1% by weight 1,2-dichloroethane solution, was 0.068.

EXAMPLE 15

9 Grams (0.0160 moles) of 2-ethylenediamino-4,6-bis-[(2',2',6',6'-tetramethyl-piperidin-4'-yl)-butylamino]-1,3,5-triazine were dissolved in 100 ml of DMF, in which 2.20 g (0.018 moles) of potassium carbonate had been suspended.

Then, under stirring, 1.40 g (0.008 moles) of 1,4-dichloromethyl-benzene were added dropwise, in 10 minutes, under stirring. The reaction mixture was heated to 90° C., stirred for 5 hours, then cooled to 20° C., then 1.75 g (0.00751 moles) of 4-bromomethyl benzoyl chloride were added dropwise in 30 minutes, under stirring. After the slight exothermia of the reaction was over, stirring was maintained for 5 hours at 20° C. After the usual recovering and purification operations, a pale violet resin with m.p. 147°–156° was obtained, whose viscosity in a 1% by weight 1,2-dichloroethane solution was 0.082.

EXAMPLE 16

300 Grams polypropylene (Moplen F 020 produced by Messrs. Montedison), 0.6 g calcium stearate and 0.6 g n-octadecyl-3-(3,4-di-ter-butyl-5-hydroxyphenyl)propionate were mixed with 0.75 g of a stabilizer, described in the foregoing examples, dissolved in 30 ml acetone. The solvent was then removed in vacuo at 50° C.

The dry mixture was then additionally mixed and homogenized in a mixer at a temperature of 200° C. for 10 minutes. The resulting composition was converted, by pressure at 260° C., into films 0.2 mm thick. Samples were cut from these films and irradiated with UV light in a Xenotest 150. The irradiated samples were periodically examined in infrared light, determining the increase with time in the carbonyl band at 5.85μ compared with a sample not containing light stabilizer compounds. The time (T 0.1) necessary for obtaining an increase of 0.1 in the extinction of carbonyl was determined.

The results are illustrated in Table 2.

TABLE 2

| Stabilizer | T 0.1 (hours) |
|---|---|
| Without stabilizer | 300 |
| Compound from Example 1 | >1000 |
| Compound from Example 2 | >1000 |
| Compound from Example 3 | >1000 |
| Compound from Example 4 | >1000 |
| Compound from Example 6 | >1000 |
| Compound from Example 7 | >1000 |
| Compound from Example 10 | >1000 |
| Compound from Example 12 | >1000 |

EXAMPLE 17

300 Grams of high-density polyethylene (Moplen RO produced by Messrs. Montedison), 0.9 g of n-octadecyl-3-(3,5-tert.butyl-4-hydroxy-phenyl)-propionate and 0.3 g calcium stearate were mixed with 0.6 g of a stabilizer described in the foregoing examples, dissolved in 30 ml acetone.

After the solvent had been removed in vacuo at 50° C., the dry mixture was additionally mixed and homogenized at 190° C. in a mixer. The resulting composition was converted, by pressure at 200° C., into films as described in Example 11, the time necessary to obtain an increase of 0.05 in the extinction of carbonyl being determined.

The results are illustrated in Table 3.

TABLE 3

| Stabilizer | T 0.05 (hours) |
|---|---|
| Without stabilizer | 350 |
| Compound from Example 1 | >1500 |
| Compound from Example 2 | >1500 |
| Compound from Example 3 | >1500 |
| Compound from Example 4 | >1500 |
| Compound from Example 5 | >1500 |
| Compound from Example 7 | >1500 |
| Compound from Example 10 | >1500 |
| Compound from Example 12 | >1500 |

We claim:

1. Compounds having the general formula I

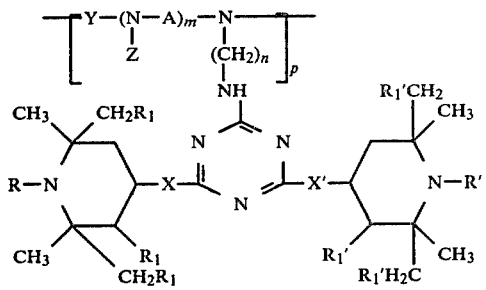

in which R and R' can be the same or different, and represent hydrogen, a straight-chain or branched-chain alkyl radical having 1 to 12 carbon atoms, an alkenyl radical having 3 to 8 carbon atoms, an aralkyl radical having 7 to 19 carbon atoms;

$R_1$ and $R'_1$ can be the same or different and represent hydrogen or methyl;

X and X' can be the same or different and represent oxygen or the group $N-R_2$ in which $R_2$ represents hydrogen, straight-chain or branched-chain alkyl having 1 to 12 carbon atoms, a cycloalkyl radical having 5 to 12 carbon atoms, an aralkyl radical having 7 to 12 carbon atoms;

n can be 2 to 12;

A represents $-(CH_2)_n-$, in which n has the previously defined meaning, the group:

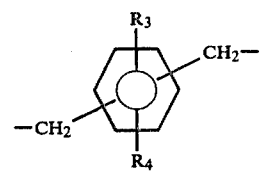

in which $R_3$ and $R_4$ are hydrogen or methyl, the group

the group

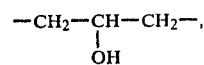

the group $-CH_2-CH_2-(O-CH_2-CH_2)_a-$ in which a can be 1-3;

Z represents hydrogen, an alkyl radical having 1 to 18 carbon atoms, a group of formula II (II)

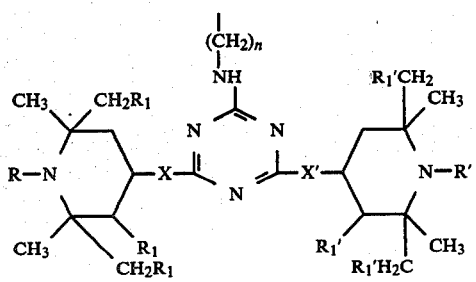

in which R, R', R$_1$, R'$_1$, X, X' and n have the previously defined meaning, or a piperidine group of formula III

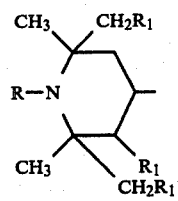

m can be equal to zero or 1;
Y, when m is zero, has the same meaning of A; when m is 1, can have the same meaning of A or represent the following groups

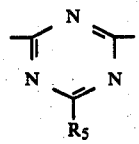

—CO—R$_6$—CO; —CO—NH—R$_7$—NH—CO, —COO—R$_8$—OOC—, —H$_2$C—R$_9$—CO—, in which R$_5$ represents hydrogen, a straight-chain or branched alkyl radical having 1 to 18 carbon atoms, a cycloalkyl radical having 5 to 12 carbon atoms, an alkenyl radical having 3 to 18 carbon atoms, an optionally substituted aralkyl radical, having 7 to 19 carbon atoms, an aryl radical having 6 to 12 carbon atoms or the

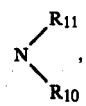

O—R$_{11}$, S—R$_{11}$ groups, in which R$_{11}$ and R$_{10}$ can be the same or different and represent hydrogen, a straight-chain or branched alkyl radical having 1 to 18 carbon atoms, a cycloalkyl radical having 5 to 12 carbon atoms, an aralkyl radical having 7 to 12 carbon atoms, an aryl radical having 6 to 12 carbon atoms, R$_{11}$ and R$_{10}$ together with the nitrogen atom can form a 5 to 7 membered heterocyclic ring; or R$_5$ represents the piperidine group of formula IV

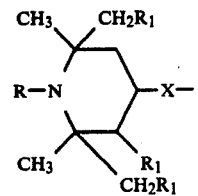

in which R, R$_1$ and X have the previously defined meaning;
R$_6$ represents a bivalent alkylene radical having 1 to 8 carbon atoms, the phenylene radical;
R$_7$ represents a bivalent alkylene radical having 2 to 6 carbon atoms, the tolylene radical, the xylene radical;
R$_8$ represents a bivalent alkylene radical having 2 to 8 carbon atoms;
R$_9$ represents an alkylene radical having 1 to 2 carbon atoms or a p-phenylene radical;
p can vary from 2 to 2000.

2. Compounds according to claim 1 of formula V

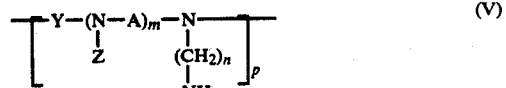
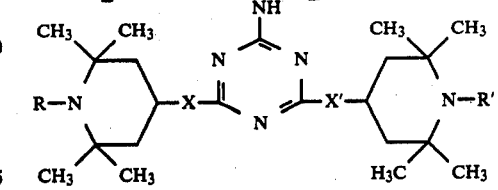

in which Y, Z, A, m, n, R, R', X, X', p have the meaning as as defined in claim 1.

3. Compounds according to claim 1 of formula X

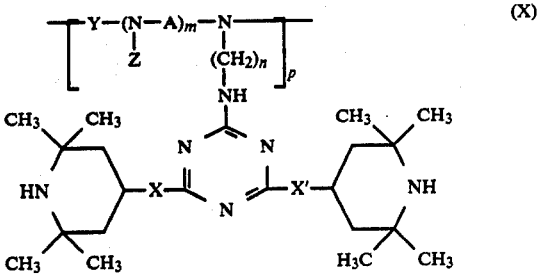

in which Y, Z, A, m, n, X, X' and p have the meaning as defined in claim 1.

4. Compounds according to claim 1 of formula XI

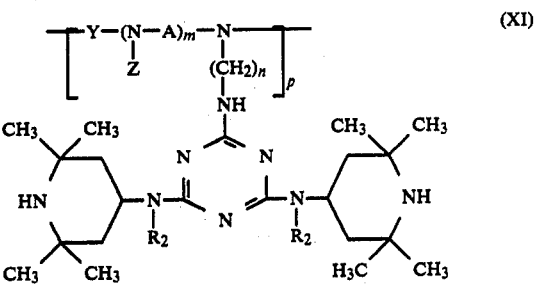

in which Y, A, Z, m, n, R₂ and p have the meaning as defined in claim 1.

5. Compounds according to claim 1 of formula XII

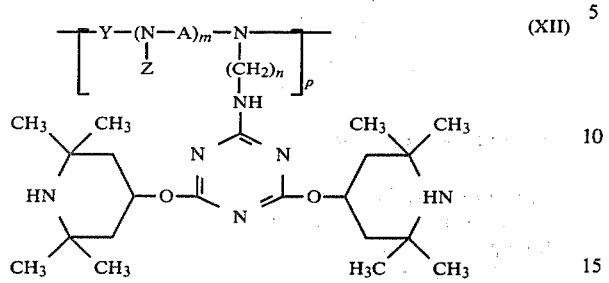

in which Y, Z, A, m, n and p have the meaning as defined in claim 1.

6. Compounds according to claim 1 of formula XIII

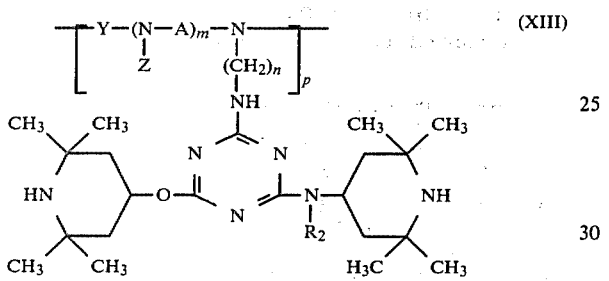

in which Y, Z, A, R₂, m, n and p have the meaning as defined in claim 1.

7. Compounds according to claim 1 of formula XIV

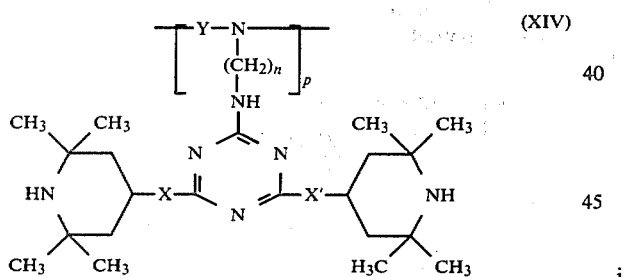

in which n, X, X′, p and Y have the meaning as defined in claim 1 when m is zero.

8. Compounds according to claim 1 of formula XV

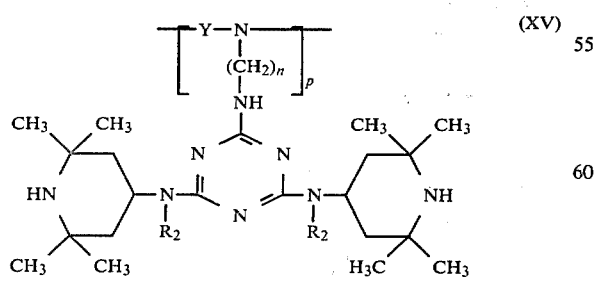

in which n, R₂, p and Y have the meaning as defined in claim 1 when m is zero.

9. Compounds according to claim 1 of formula XVI

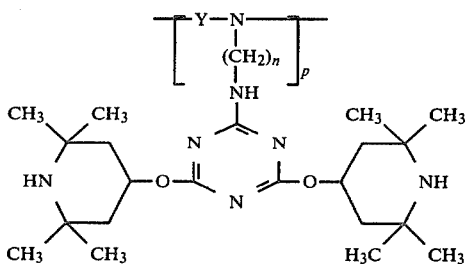

in which n, p and Y have the meaning as defined in claim 1 when m is zero.

10. Compounds according to claim 1 of formula XVII

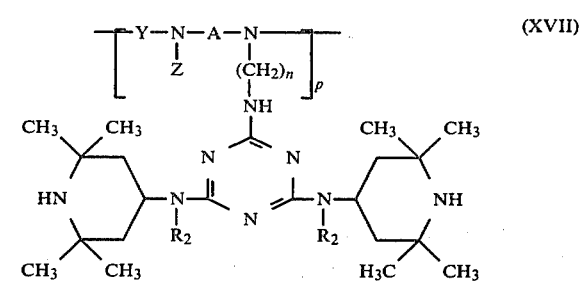

in which Y, Z, A, n, R₂ and p have the meaning as defined in claim 1.

11. Compounds according to claim 1 of formula XVIII

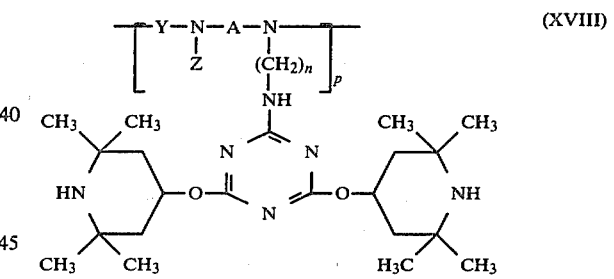

in which Y, Z, A, n and p have the meaning as defined in claim 1.

12. Compounds according to claim 1 of formula XIX

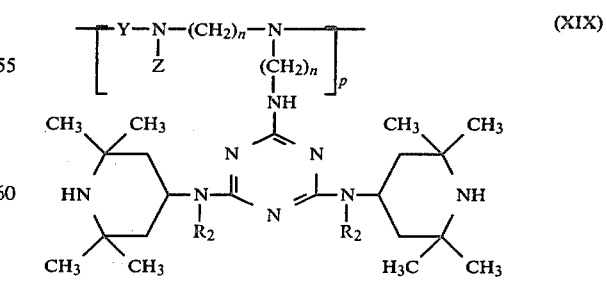

in which n can be 2 or 3; Y, Z, R₂ and p have the meaning as defined in claim 1.

13. Compounds according to claim 1 of formula XX

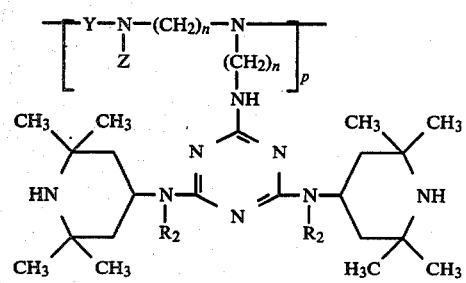

in which Z is hydrogen or the group of formula II, n can be 2 or 3, Y and $R_2$ and p have the meaning defined in claim 1.

14. A method of preparing compounds having the formula I according to claim 1, characterized in that
(a) one mole of a disubstituted triazine having the formula VI

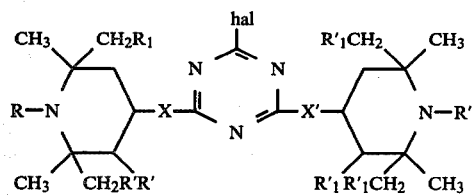

is reacted with an excess of a diamine of formula $H_2N-(CH_2)_n-NH_2$, to give compound of formula (VII)

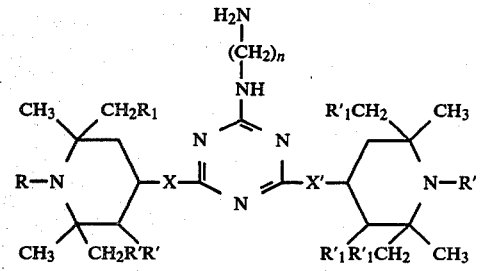

which by subsequent reactions with hal—A—hal, depending on the ratios, give compounds of formula I or intermediates of formula VIII

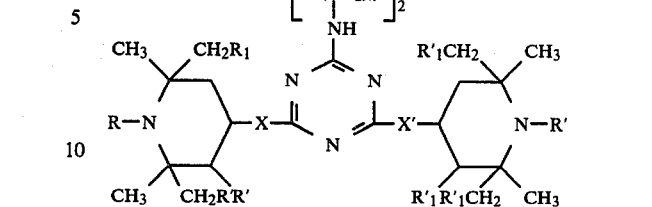

which by their turn, by subsequent reaction with hal—Y—hal give compounds of formula I, or
(b) compound VI is reacted with an amine of formula

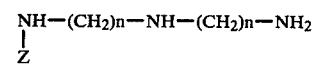

to give compounds of formula IX

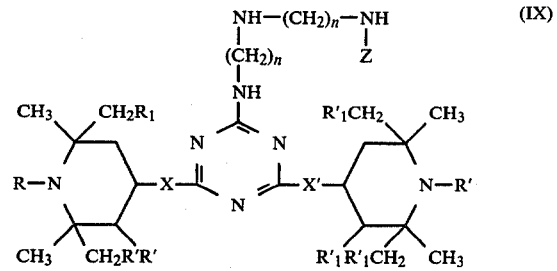

which, by reaction with hal—Y—hal, give compounds of formula I; the various designations having the meanings as set forth in claim 1.

15. A method of stabilizing a polymer against the deteriorating effects of heat, sunlight and oxygen which comprises incorporating in the polymer an effective amount of a compound according to claim 1.

16. A method according to claim 15 in which the compound according to claim 1 is present in an amount of about 0.01 to about 5.0% on the weight of the polymer.

17. A method according to claim 16 in which the polymer is polyethylene or polypropylene.

* * * * *